United States Patent
Jaeger et al.

(10) Patent No.: US 9,636,460 B1
(45) Date of Patent: May 2, 2017

(54) PNEUMATIC AUTOINJECTOR WITH AUTOMATED MIXING

(71) Applicant: Creare LLC, Hanover, NH (US)

(72) Inventors: Michael D. Jaeger, Plainfield, NH (US); Mark C. Bagley, Grafton, NH (US); Roger W. Hill, Grantham, NH (US); Sandra J. Graveson, Enfield, NH (US); Robert T. Payne, Montpelier, VT (US)

(73) Assignee: Creare LLC, Hanover, NH (US)

( * ) Notice: Subject to any disclaimer, the term of this patent is extended or adjusted under 35 U.S.C. 154(b) by 0 days.

(21) Appl. No.: 15/392,200

(22) Filed: Dec. 28, 2016

(51) Int. Cl.
*A61M 5/32* (2006.01)
*A61M 5/20* (2006.01)
(Continued)

(52) U.S. Cl.
CPC ........ *A61M 5/2066* (2013.01); *A61M 5/2033* (2013.01); *A61M 5/2053* (2013.01); *A61M 5/3146* (2013.01); *A61M 5/31566* (2013.01); *A61M 5/31578* (2013.01); *A61M 5/31591* (2013.01); *A61M 5/31596* (2013.01); *A61M 5/322* (2013.01); *A61M 5/3287* (2013.01);
(Continued)

(58) Field of Classification Search
CPC .............. A61M 5/2066; A61M 5/2033; A61M 5/31596; A61M 5/31591; A61M 5/3146; A61M 5/31566; A61M 5/2053; A61M 5/31578; A61M 5/3287; A61M 5/322; A61M 2202/02; A61M 2202/04; A61M 2202/06; A61M 2005/206; A61M 2005/208; A61M 2005/2026; A61M 2005/582; A61M 2205/581
See application file for complete search history.

(56) References Cited

U.S. PATENT DOCUMENTS 4,031,889 A  6/1977  Pike
5,176,645 A  1/1993  Guerrero
(Continued)

FOREIGN PATENT DOCUMENTS

EP  0937475 A2  8/1999
EP  1464351 B1  1/2007
(Continued)

*Primary Examiner* — Andrew Gilbert
*Assistant Examiner* — Amber Stiles
(74) *Attorney, Agent, or Firm* — Downs Rachlin Martin PLLC

(57) ABSTRACT

A pneumatic autoinjector that, once activated, automatically mixes at least two components in a pre-filled chamber and then ejects the mixture in a manner suitable for medicament injection. The mixable components may be a dry/wet combination (e.g., powder and solvent), wet/wet combination (e.g., two pre-diluted medicaments), wet/gas combination (e.g., chemical A and gas B), or gas/gas combination. In some embodiments, autoinjectors made in accordance with the teachings of the present disclosure may automatically perform a sequence comprising thorough medicament mixing (e.g., reconstitution of a dried medicament with solvent), an optional pause to enhance medicament dissolution or suspension, optional needle insertion into the patient (not required in needle-free embodiments), medicament injection into the patient, and optional needle retraction for safe storage.

18 Claims, 14 Drawing Sheets

(51) Int. Cl.
*A61M 5/315* (2006.01)
*A61M 5/31* (2006.01)

(52) U.S. Cl.
CPC . *A61M 2005/206* (2013.01); *A61M 2005/208* (2013.01); *A61M 2005/2026* (2013.01); *A61M 2202/02* (2013.01); *A61M 2202/04* (2013.01); *A61M 2202/06* (2013.01); *A61M 2205/581* (2013.01); *A61M 2205/582* (2013.01)

(56) References Cited

U.S. PATENT DOCUMENTS

| | | |
|---|---|---|
| 5,300,030 A | 4/1994 | Crossman et al. |
| 6,270,479 B1 | 8/2001 | Bergens et al. |
| 6,599,272 B1 | 7/2003 | Hjertman et al. |
| 7,654,983 B2 | 2/2010 | De La Sema et al. |
| 7,695,449 B2 | 4/2010 | Wang et al. |
| 7,699,804 B2 | 4/2010 | Barry et al. |
| 7,749,194 B2 | 7/2010 | Edwards et al. |
| 8,496,621 B2 | 7/2013 | Basso et al. |
| 8,870,821 B2 | 10/2014 | Laufer |
| 9,173,999 B2 | 11/2015 | Edwards et al. |
| 9,199,037 B2 | 12/2015 | Buchine et al. |
| 2003/0105430 A1 | 6/2003 | Lavi et al. |
| 2008/0103490 A1* | 5/2008 | Edwards ............... A61M 5/19 604/890.1 |
| 2013/0317477 A1 | 11/2013 | Edwards et al. |
| 2014/0094776 A1 | 4/2014 | Cronenberg |
| 2015/0250953 A1 | 9/2015 | Elmen |

FOREIGN PATENT DOCUMENTS

| | | |
|---|---|---|
| WO | 2015165757 | 11/2015 |
| WO | 2016058009 | 4/2016 |

\* cited by examiner

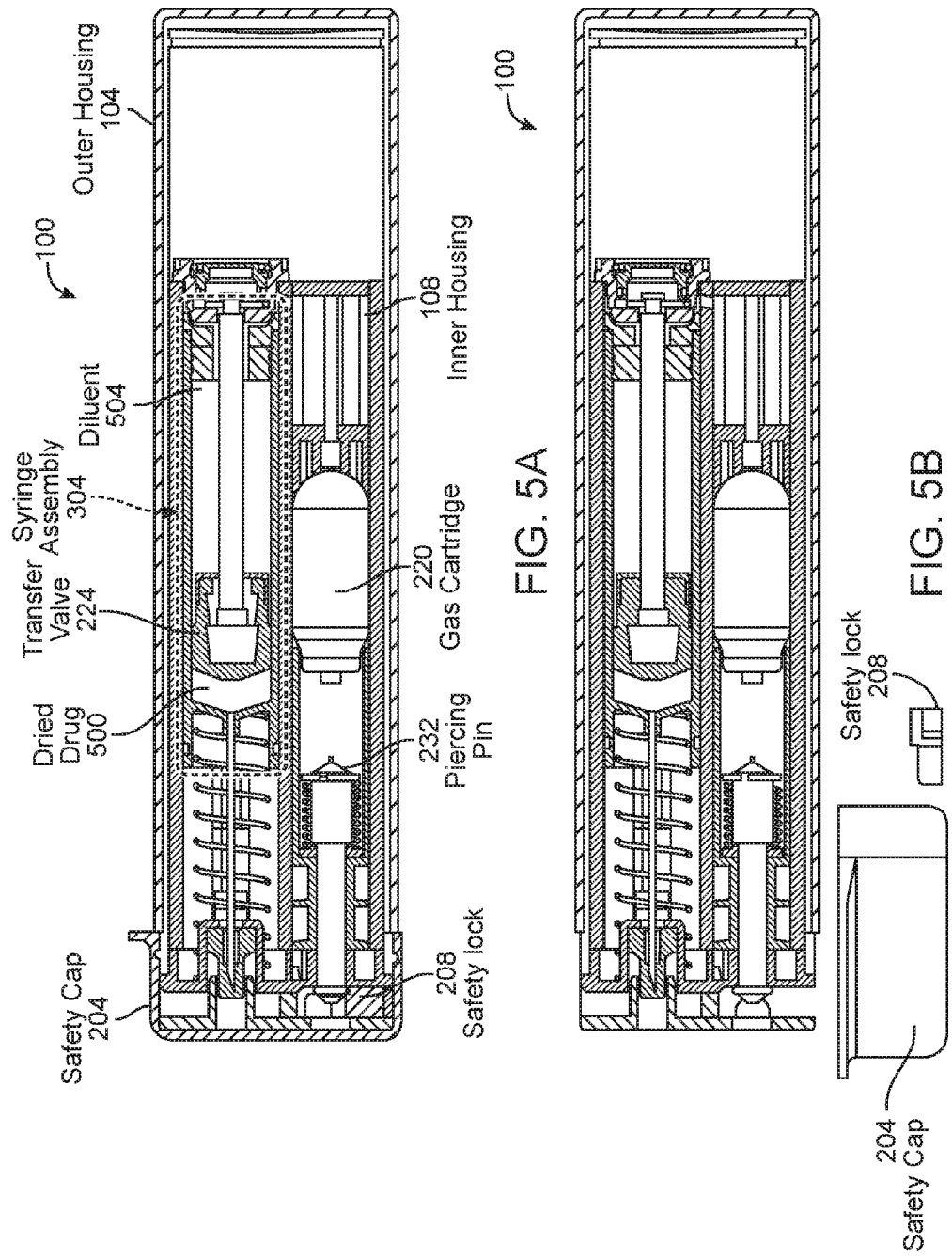

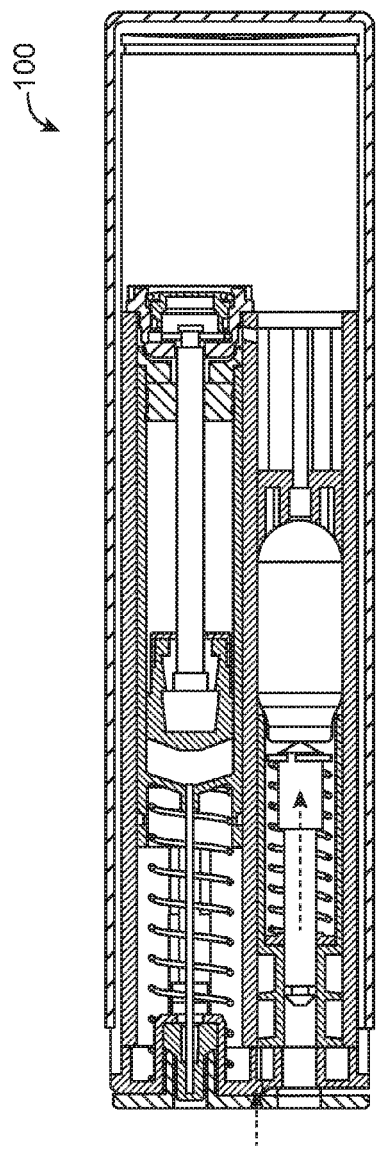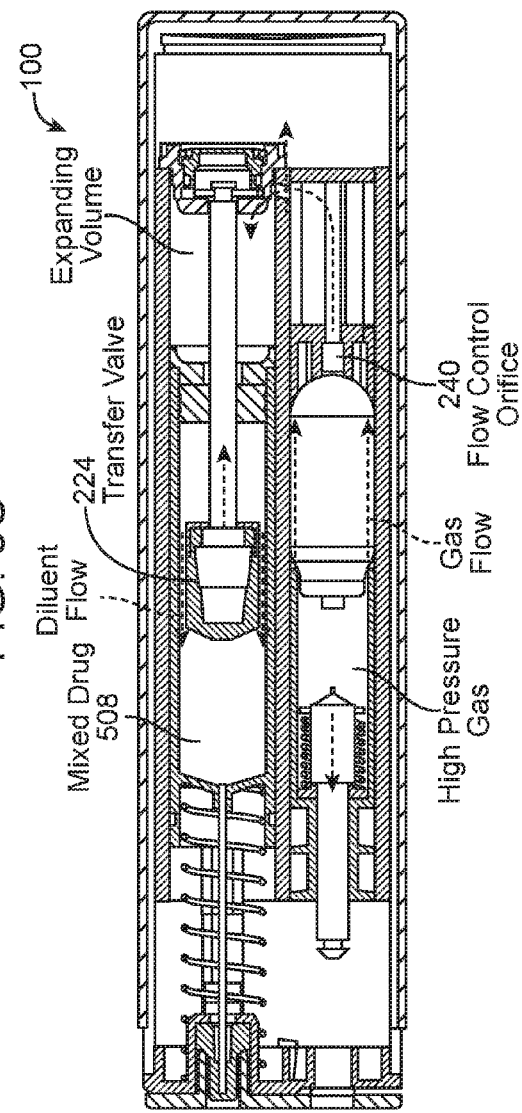

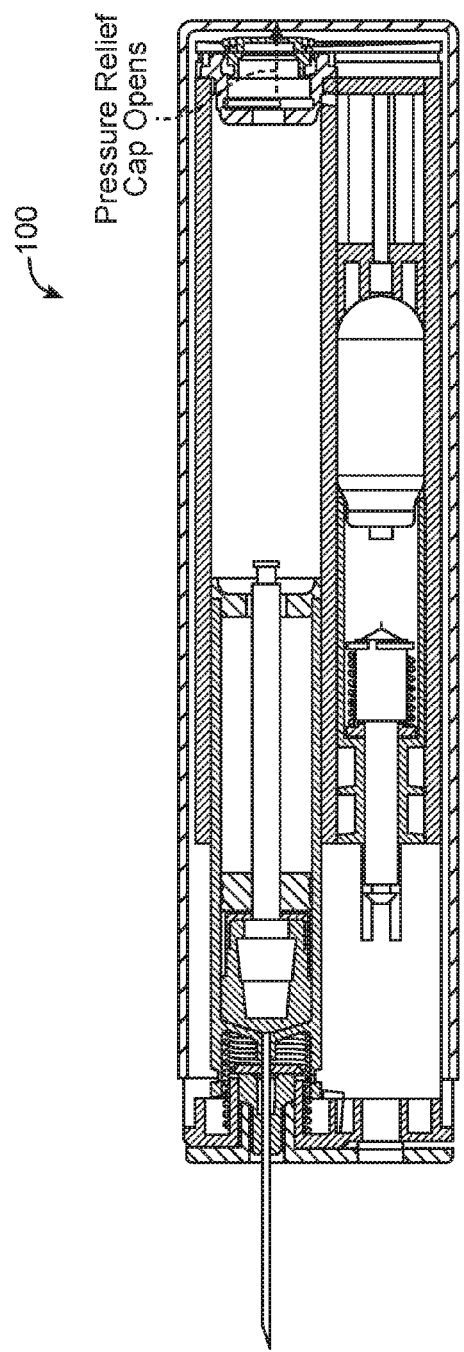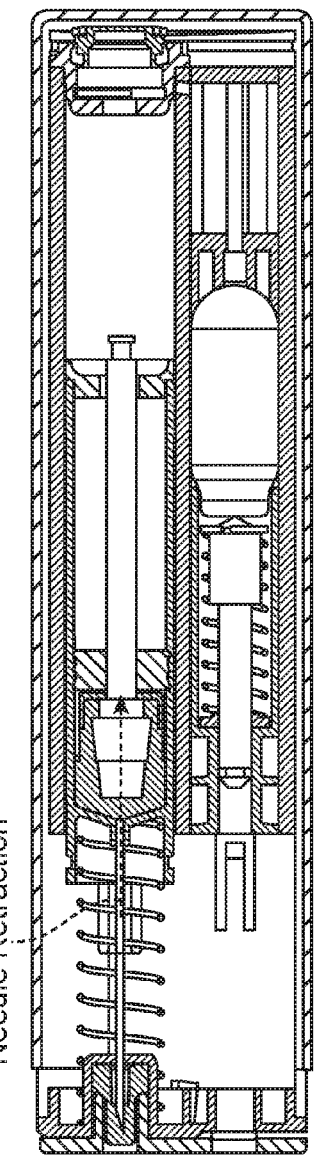
FIG. 5G
FIG. 5H

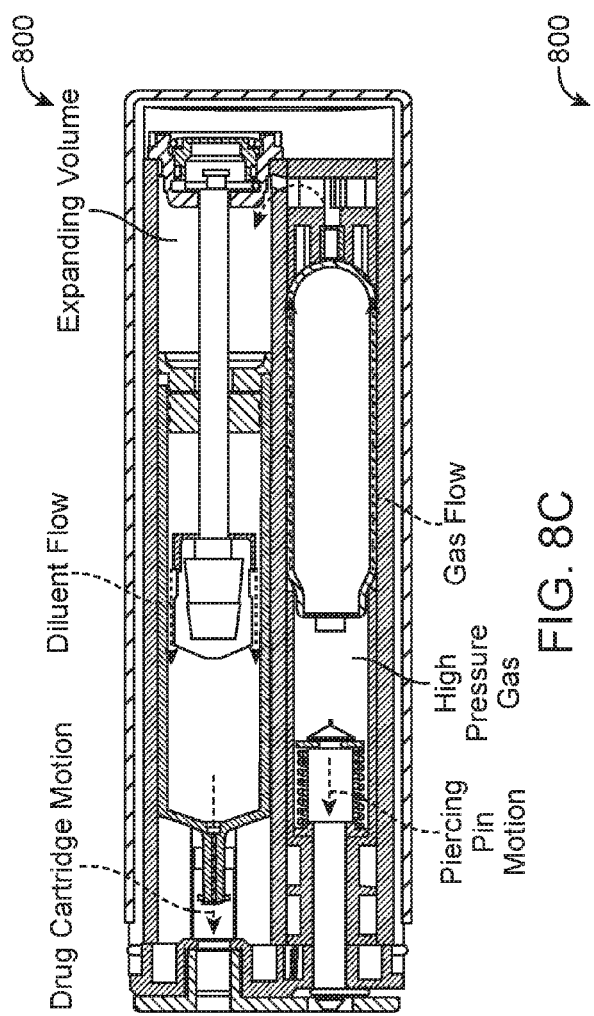
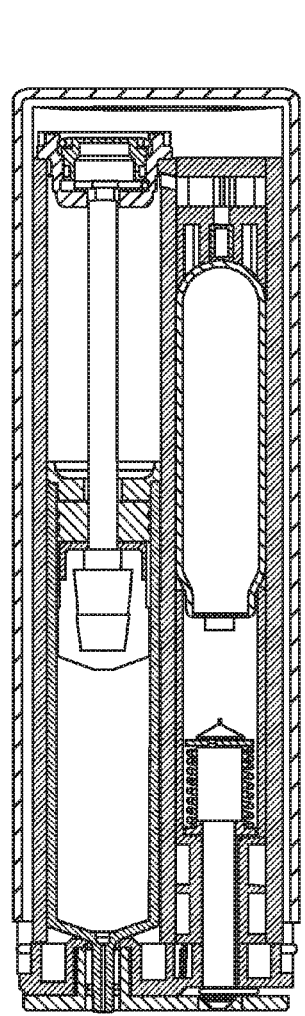
FIG. 8C
FIG. 8D

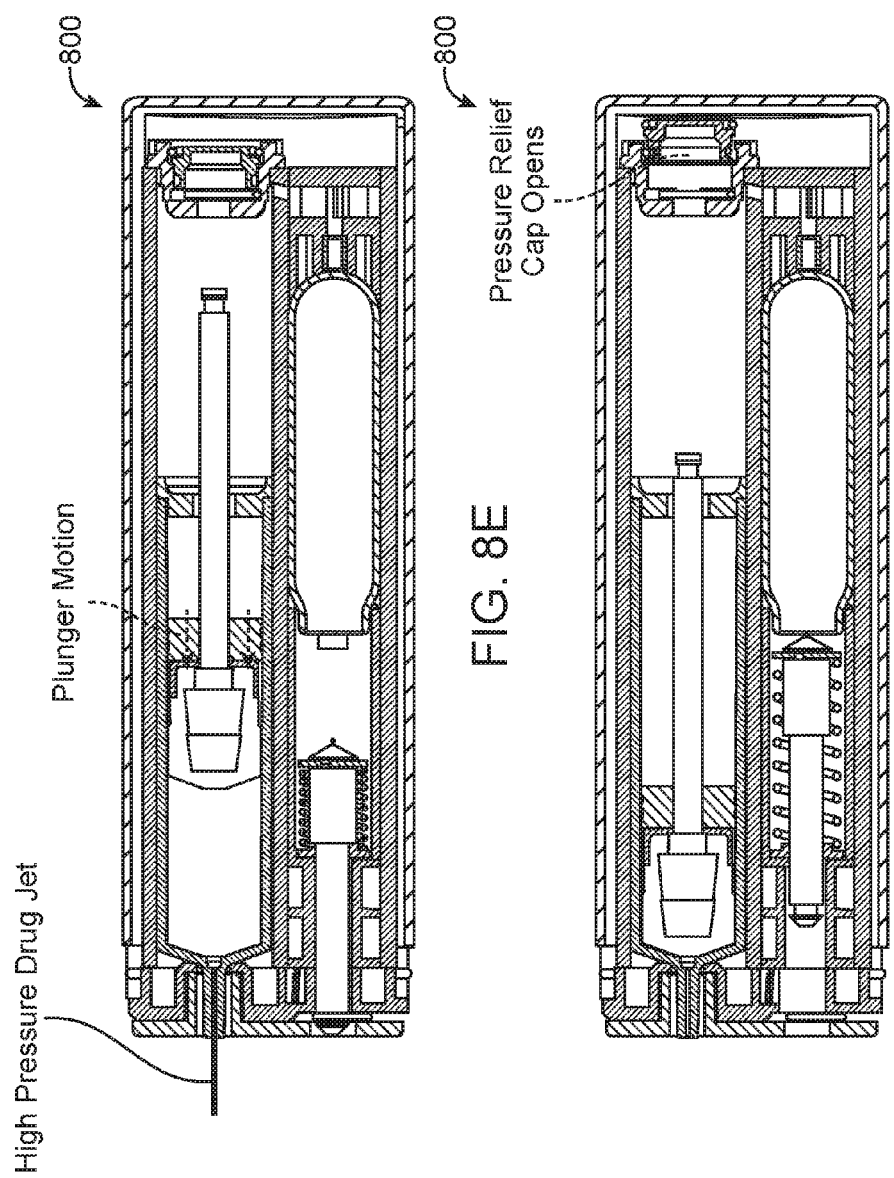

US 9,636,460 B1

PNEUMATIC AUTOINJECTOR WITH AUTOMATED MIXING

STATEMENT REGARDING FEDERALLY SPONSORED RESEARCH OR DEVELOPMENT

This invention was made with government support under SBIR Contract No. W911QY-14-C-0047 awarded by the U.S. Army. The government has certain rights in the invention.

FIELD OF THE INVENTION

The present invention generally relates to the field of automatic injection devices. In particular, the present invention is directed to a pneumatic autoinjector with automated mixing.

BACKGROUND

Various automatic injectors, or autoinjectors, have been developed that are capable of either administering emergency first aid antidotes in cases of chemical, biological, and toxin (CBT) attacks or delivering emergency first aid medicaments to abate symptoms of medical conditions such as anaphylactic shock. Conventional autoinjectors are limited in their usefulness, as, in many instances, they require storing medicaments in diluted form within the autoinjector, which limits the shelf life of many medicaments and the autoinjectors that contain them. Storing medicaments or vaccines in dried form separate from the diluent can, in many cases, significantly improve the stability and shelf life of the medicament or vaccine. However, manually reconstituting a dried medicament or vaccine immediately prior to injection is a complex process, typically reserved for medical professionals. As such, further innovation in the field of autoinjectors is needed in order to enable emergency autoinjectors to store medicaments or vaccines in dried form separate from the diluent and mix the dried drug and diluent immediately prior to injection. In addition, innovations are needed to simplify usage of such automixing autoinjectors and eliminate the need for certain autoinjectors to be administered by medical professionals. Such automixing autoinjectors could also provide long term storage and delivery of multicomponent medicament mixtures that cannot be stored long term as a single diluted mixture, such as for example two different diluted medicaments, a diluted medicament and a dried medicament, or a dried mixture of two different medicaments and a single diluent.

SUMMARY OF THE DISCLOSURE

In one implementation, an automatic injector, or autoinjector, for delivering a medicament is provided. The autoinjector includes an outer housing having proximal and distal ends; an inner housing disposed within the outer housing, the inner housing containing an activation channel and a medicament channel, the activation and medicament channels having proximal and distal ends and the inner housing having a cross-channel coupling located proximate the distal ends of the activation and medicament channels that fluidly couples the activation and medicament channels; an activation mechanism; and an activation impeding mechanism, the activation channel comprising: a pressure-release mechanism associated with an activation spring; a flow control coupling located proximate the distal end of the activation channel and fluidly coupled with the medicament channel; and a pressurizable chamber containing compressed gas, and the medicament channel comprising: a pull rod retainer and a pressure-relief mechanism located at the distal end of the medicament channel; and a medicament housing assembly including a medicament delivery mechanism and a medicament housing body slidably disposed within the medicament channel, the medicament housing body including proximal and distal ends and comprising: a medicament chamber fluidly coupled with the medicament delivery mechanism and having proximal and distal ends; a valve disposed within the medicament chamber and separating two substances predisposed within the medicament chamber; a pull rod disposed within the medicament housing body and having proximal and distal ends, the distal end of the pull rod releasably coupled with the pull rod retainer and the proximal end of the pull rod coupled with the valve; and a plunger sealingly disposed about the pull rod within the medicament housing body.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIGS. 5A-H are cross-sectional plan views of the pneumatic autoinjector of FIG. 1, illustrating various stages of its operation;

FIGS. 8A-F are cross-sectional plan views of an example of a needle-free pneumatic autoinjector implemented in accordance with aspects of the present disclosure, illustrating various stages of its operation.

DETAILED DESCRIPTION

Figure 1:
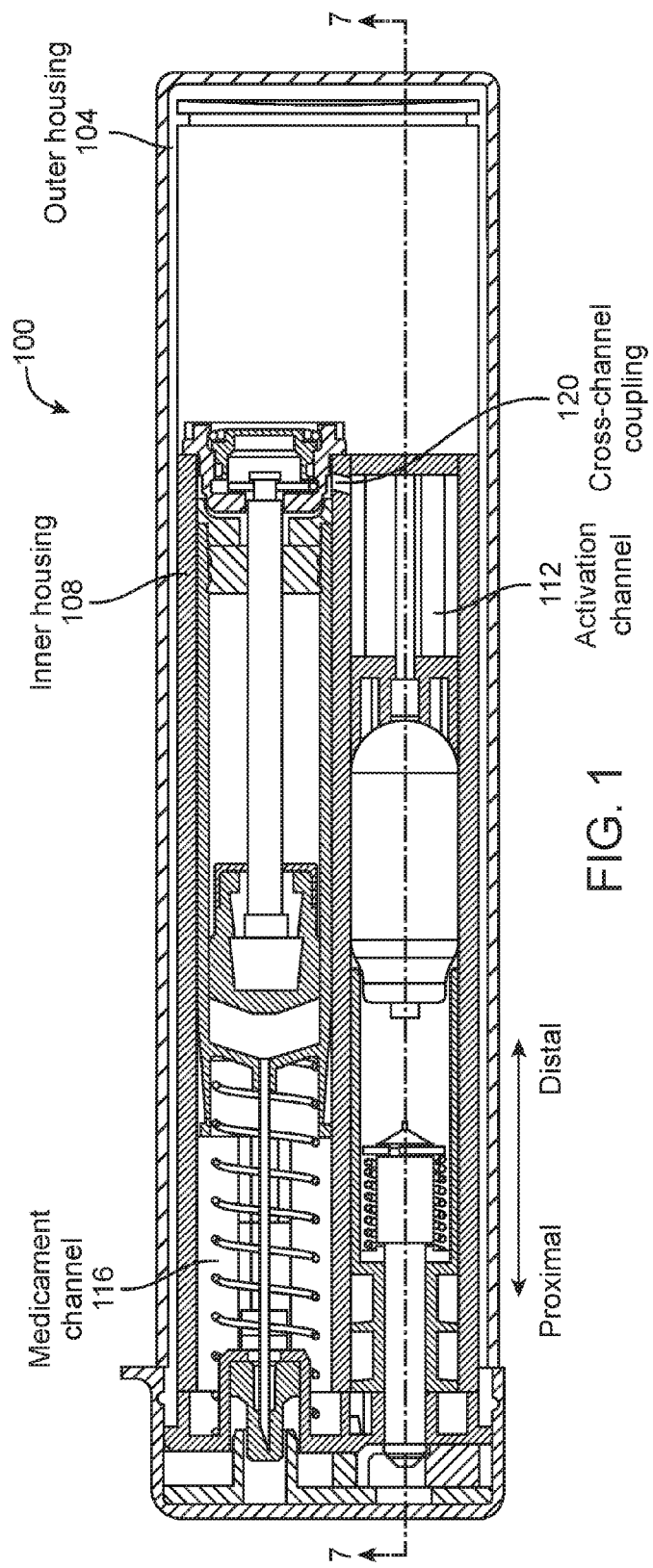
FIG. 1 is a cross-sectional plan view of an example of a pneumatic autoinjector with automated mixing capabilities implemented in accordance with aspects of the present disclosure.

Emergency medical autoinjectors should be small enough to carry with daily gear, low cost to enable wide distribution and stockpiling, and simple enough for use by nonmedical personnel. Suitability for use by nonmedical personnel generally requires that an autoinjector can be operated by a simple "arming" action followed by a single, simple triggering or activation action, after which all processes of the injection are automatically performed without additional user action. Additionally, autoinjectors for emergency use must be very simple to hold and use, since the user may be partially or severely impaired while trying to operate the device.

Long shelf life is also important for emergency autoinjectors, since replacing expired autoinjectors can be expensive and present significant logistical considerations for military, government, and civilian stockpiles. Many medicaments have greatly shortened shelf life due to oxidation, protein degradation, or other adverse reactions when stored in diluted form. Storing such medications in an autoinjector in dried form, separate from the diluent, until the time of use can thus provide autoinjectors with greatly extended shelf life. Medicaments such as dried drugs or vaccines stored in dried form for extended shelf life are commonly reconstituted in a vial, withdrawn using a syringe, and then injected at the proper dose by trained medical personnel, but this manual approach is not feasible for emergency medicament administration by nonmedical personnel. Existing medicament autoinjectors can be used to store and mix or sequentially inject two or more diluted medicaments, but drug reconstitution is more challenging. Some manually mixed dual chamber syringes and autoinjectors that can perform medicament reconstitution require several user-actuated or user-performed steps, such as shaking to mix, and are thus generally suitable for use only by trained medical personnel. Current fully automated autoreconstituting autoinjectors cannot provide vigorous mixing to ensure breakup of caked medicaments and the mixing time cannot be tuned prior to delivery to ensure thorough dissolution or suspension of medicaments with low solubility.

In order to enable the advantages of extended shelf life and thorough medicament reconstitution in an emergency autoinjector, the present inventors have developed an autoinjector capable of automatically and thoroughly mixing a dried medicament with a diluent, providing an optional brief pause for improved medicament dissolution and homogenization, and, in some embodiments, inserting a needle into a patient, injecting the mixed medicament, and then retracting the needle, all without requiring the user to perform additional steps beyond arming and triggering the device. By hiding the needle from sight during the entire sequence in embodiments that use a needle as a medicament delivery mechanism, needle-sensitive users can be prevented from seeing the needle, which can help to minimize stress. Further, as the needle is retracted after injection, needle-stick injuries can be prevented.

Aspects of the present disclosure provide a pneumatic autoinjector that, once activated, automatically mixes at least two components in a pre-filled chamber and then ejects the mixture in a manner suitable for medicament injection. Notably, although aspects of the disclosure are directed to autoinjectors for medicaments, substances other than medicaments, such as epoxies, may be mixed and injected or otherwise extruded using a device incorporating one or more aspects of the present disclosure. The mixable components may be a dry/wet combination (e.g., powder and diluent), wet/wet combination (e.g., two diluted medicaments), wet/gas combination (e.g., chemical A and gas B), or gas/gas combination. In some embodiments, autoinjectors made in accordance with the teachings of the present disclosure may automatically perform a sequence comprising thorough medicament mixing (e.g., reconstitution of a dried medicament with diluent), an optional pause to enhance medicament dissolution or suspension, optional needle insertion into the patient (not required in needle-free embodiments), medicament injection into the patient, and optional needle retraction for safe storage.

Figure 2:
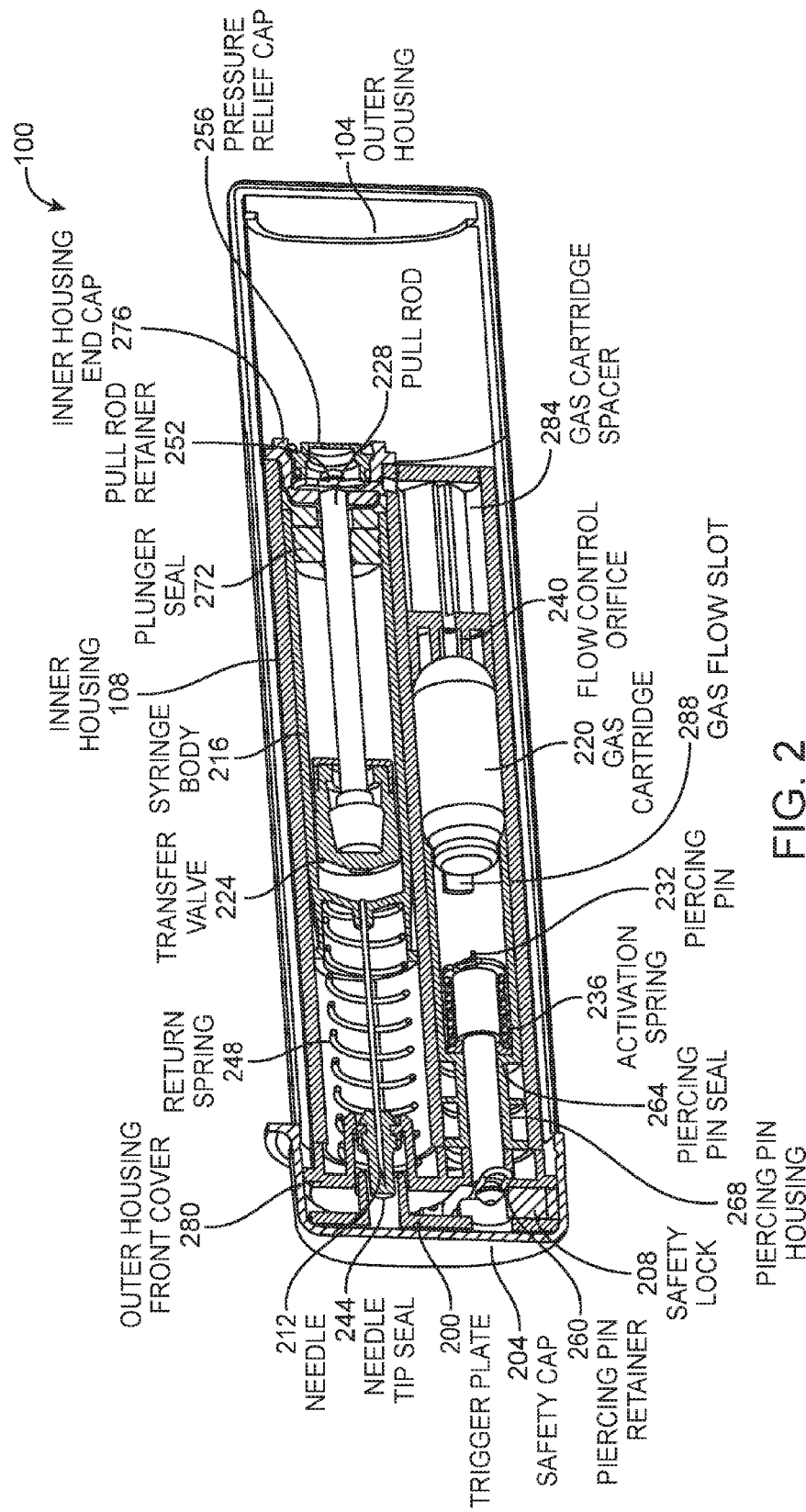
FIG. 2 is a cross-sectional perspective view of the pneumatic autoinjector of FIG. 1.
Figure 3:
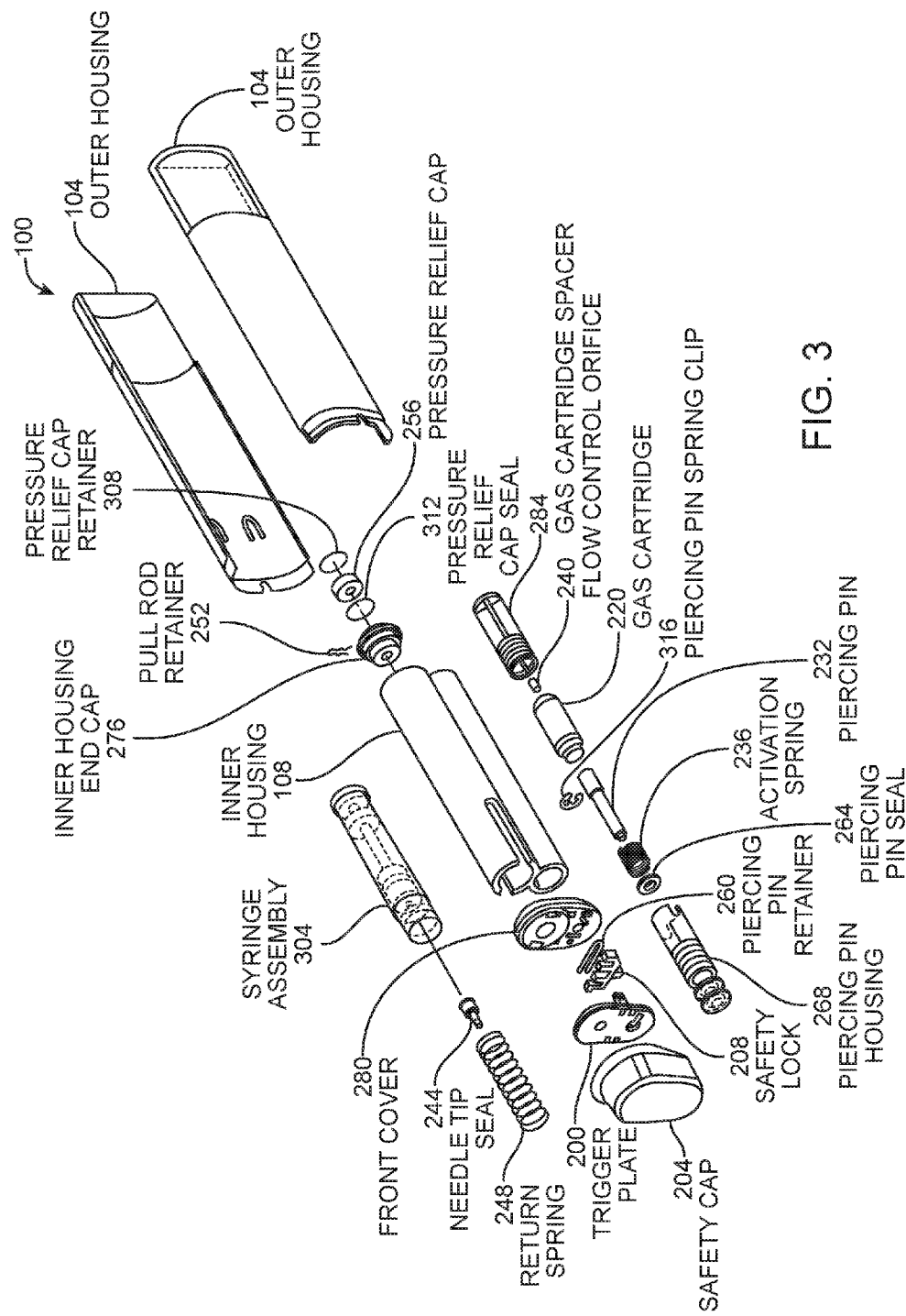
FIG. 3 is an exploded view of the pneumatic autoinjector of FIG. 1.
Figure 4:
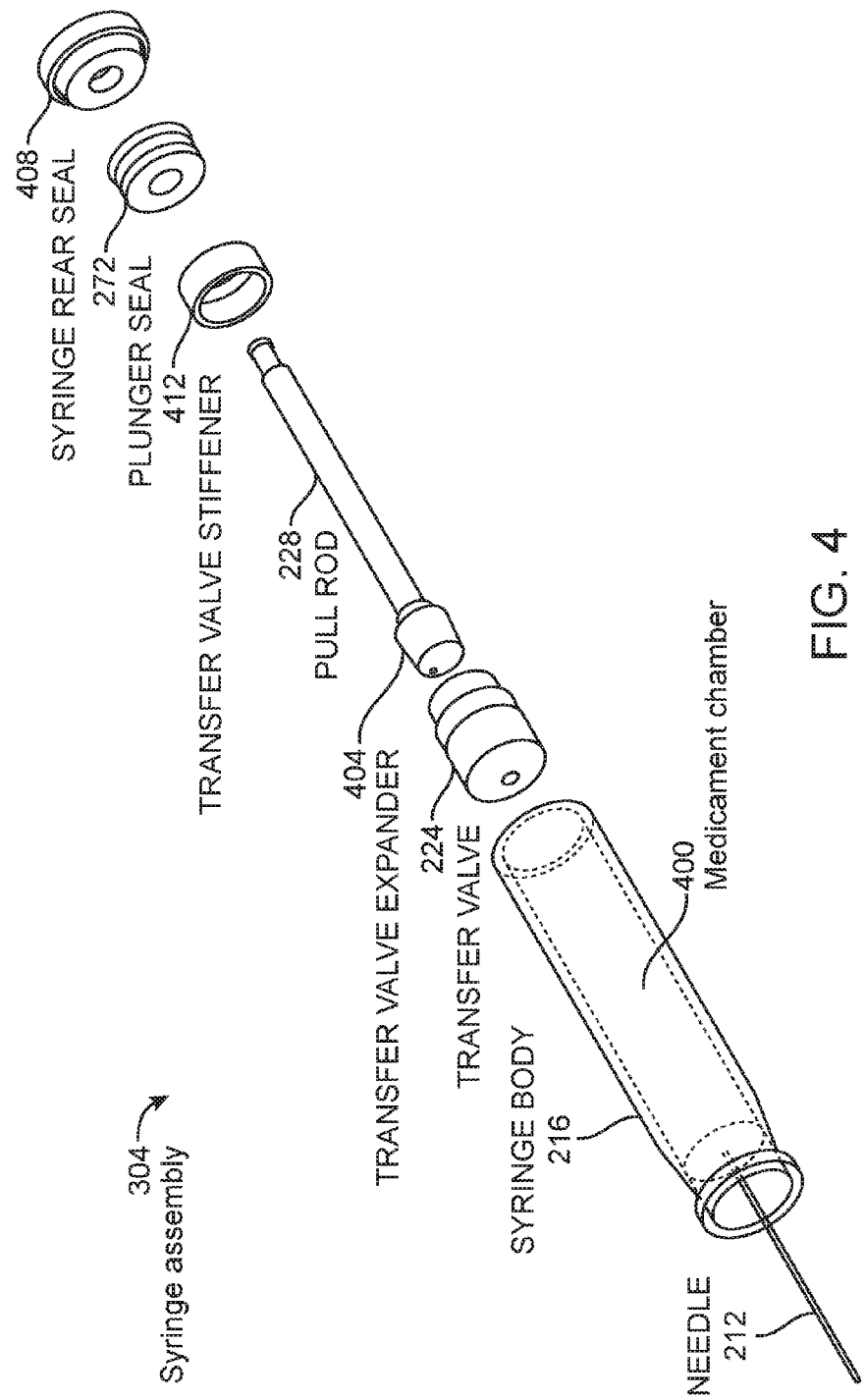
FIG. 4 is an exploded view of the syringe assembly of the pneumatic autoinjector of FIG. 1.

FIG. 1 illustrates a pneumatic autoinjector 100 comprising a plurality of components, shown in detail in FIGS. 2-4, that work in concert to mix and deliver a medicament on demand. The part actions within autoinjector 100 that cause medicament injection and needle retraction are initiated by a force applied by a user to an activation mechanism, here a trigger plate 200, on a proximal end of the autoinjector. Thereafter, the internal parts movement is automatically and sequentially performed by the forces applied by a combination of two springs and the gas released from a high-pressure gas cartridge, as further described hereinbelow. The timing of events is determined by various tunable aspects of the autoinjector further described hereinbelow, including the sizing of components such as various gas volumes and a metering flow control orifice, the size and charge pressure of a compressed gas cartridge, and the triggering pressures of pressure-actuated release mechanisms. Autoinjector 100 has an outer housing 104 adapted to receive a removable safety cap 204 on a proximal end of the housing that is designed and configured to protect trigger plate 200 and hold a spacer in the form of a safety lock 208 in place to prevent inadvertent activation. In some embodiments, a protective case may be used in addition to or in place of safety cap 204. As shown in FIG. 1, an inner housing 108, which may comprise extruded aluminum, high-strength molded plastic, and/or other materials, contains an activation channel 112 and a medicament channel 116 and is slidably disposed within outer housing 104. Inner housing 108 includes a cross-channel coupling 120 located proximate distal ends of activation channel 112 and medicament channel 116 that fluidly couples the activation and medicament channels. Cross-channel coupling 120 may comprise an orifice, a valve, an expandable bladder or portion of or portal to an expandable bladder, or any other suitable coupling, and may in some embodiments comprise a second or alternative flow control orifice.

As best shown in FIGS. 2-5A, a medicament housing syringe assembly 304 including a medicament delivery mechanism in the form of a needle 212 (which may be a hypodermic needle or other appropriate delivery mechanism) and a medicament housing syringe body 216, which may be formed from glass, metal, or plastic with an interior and/or exterior glass or metal coating, is slidably disposed within medicament channel 116, while a pressurizable chamber containing compressed gas, here a gas cartridge 220, and piercing pin components reside in activation channel 112. In this example (see, e.g., FIGS. 4 and 5A), a pre-filled medicament chamber 400 defined by syringe body 216 and fluidly coupled with needle 212 contains both a dried drug 500 and diluent 504 (e.g., solvent) separated from each other during storage by an expandable transfer valve 224 that is held firmly in place in an expanded, sealed state by a pull rod 228 with a flared front tip that acts as a transfer valve expander 404, as best illustrated in FIGS. 1-4. In some embodiments, pull rod 228 may be implemented as a piece of plastic or metal; in other embodiments, the pull rod may be implemented with or as a string, flexible filament, or tether. For details of an example of an expandable transfer valve that may be used with autoinjectors made in accordance with the present disclosure, see U.S. Pat. No. 7,699,804 to Barry, which is incorporated by reference herein for its teachings of expandable transfer valves.

As shown in FIG. 2, a pressure-release mechanism, here a piercing pin 232, is disposed within activation channel 112 and biased towards gas cartridge 220 with an activation spring 236 that provides a strong, consistent force to the piercing pin for puncturing the gas cartridge when trigger plate 200 is depressed to start an autoinjector sequence. Notably, although piercing pin 232 is used as a pressure-release mechanism and gas cartridge 220 is used as a pressurizable chamber in various embodiments described herein, other pressure-release mechanisms may be used, such as a plunger sealingly disposed within a pressurizable chamber that breaks the seal and releases the gas in the pressurizable chamber upon being actuated. Other pressure-release mechanisms may include a button, nonplanar plate, or lever, among others. Other pressurizable chambers that may be used in place of or in addition to a gas cartridge include a pressurizable chamber formed monolithically with a portion of autoinjector 100, such as activation channel 112 of inner housing 108, and chambers holding chemicals that react with the ambient air or other chemicals provided within the autoinjector to produce the pneumatic pressures required to operate the autoinjector, among others. In some embodiments, gas cartridge 220 may contain a fluid other than a gas, such as a liquefied gas. The spring-loaded activation mechanism has the advantage that a small force applied by the user is all that is necessary to trigger the device, which assures ease of use and reliability, yet the released activation spring provides a higher actuation force for reliably piercing gas cartridge 220. Additional features (see, e.g., FIGS. 1-4) include: a precision flow control coupling, here a flow control orifice 240, located proximate the distal end of activation channel 112 and fluidly coupled with medicament channel 116, which meters the high-pressure gas from gas cartridge 220 volume to the volume behind syringe assembly 304; a protective elastomer needle tip seal 244 that protects the syringe contents and keeps them sterile; a return spring 248 biasing the syringe assembly away from the proximal end of outer housing 104 in order to force retraction of needle 212 and the syringe assembly after use to conceal the needle; a pull rod retainer 252 for releasing pull rod 228 at a precisely determined pressure force; and a pressure triggered pressure relief mechanism, here a pressure relief cap 256, for venting the residual internal gas pressure at a precisely determined pressure after completion of medicament injection. Although pressure relief cap 256 is used as a pressure relief mechanism in various embodiments described herein, it may be omitted (e.g., when needle retraction is not necessary) and/or other components could be used, such as a pressure relief valve, which may apply a varying constriction as a function of the amount of time gas flows through it and/or the amount of pressure applied to it, a seal that breaks in the presence of a predetermined pressure gradient, or any other suitable mechanism, such as one or more burst disks or blow-off caps. Further, although return spring 248 is used in various embodiments disclosed herein, it may be omitted (e.g., when needle retraction is not necessary) or complemented with an extendable "pop-out" needle cover, as known in the art. Such an extendable needle cover may be, for example, retained by a detent and/or formed as a part of or in place of trigger plate 200. After trigger plate 200 and/or the extendable needle cover is depressed and the autoinjector is activated, the detent may release the cover and a spring or other biasing component may drive the cover away proximally from a proximal surface of the autoinjector in order to cover the needle in case it is withdrawn from the injection site prior to being retracted into the autoinjector. This would require the cover to have a needle orifice, as known in the art, and/or two or more portions that can surround the needle as they extend. In some embodiments, such as where a needle cover is used or needle retraction is not necessary, return spring 248 may be omitted from autoinjector 100. Further, although flow control orifice 240 is used as a flow control coupling in various embodiments disclosed herein, other components could be used, such as a pressure relief valve, which may apply a varying constriction as a function of the amount of time gas flows through it and/or the amount of pressure applied to it, a seal that breaks in the presence of a predetermined pressure gradient, or any other suitable mechanism, such as one or more burst disks or blow-off caps. Other components of autoinjector 100 shown in FIGS. 2-4 are described hereinbelow in the context of a description of various stages of operation of autoinjector 100 that may take place during an autoinjector sequence.

Operation of an Exemplary Embodiment

Autoinjector 100 is stored with safety cap 204 and safety lock 208 in place (see, e.g., FIG. 5A). To activate the sequence of events leading to medicament injection, the user removes safety cap 204 to expose trigger plate 200, as shown in FIG. 5B. In some embodiments, removing safety cap 204 also removes safety lock 208 that prevents trigger plate 200 motion prior to use (see, e.g., material connecting the safety lock and the safety cap in FIGS. 2 and 5A, which may be formed monolithically with the safety lock and safety cap, adhered to the safety lock and safety cap, or otherwise connect the lock and cap). This may be implemented, for example, by providing a piece of material connecting safety cap 204 and safety lock 208. However, in some embodiments, safety lock 208 may need to be manually removed after removing safety cap 204. The removal of safety lock 208 from autoinjector 100 "arms" the device for use. The user then forcefully presses newly exposed trigger plate 200 against an injection site (e.g., thigh muscle). The action of applied pressure against trigger plate 200 actuates the device by releasing spring-loaded piercing pin 232 from an activation impeding mechanism, here a piercing pin retainer 260 best shown in FIG. 3, which is then driven into the end of high-pressure gas cartridge 220, allowing the cartridge gas to escape (see, e.g., FIG. 5C). In this embodiment, the piercing pin retainer also holds the inner housing in place until the autoinjector is activated, and thus also secures the position of the pull rod and the transfer valve that hermetically separates the dried medicament and diluent during storage. Although piercing pin retainer 260 is used as an activation impeding mechanism in various embodiments described herein, other activation impeding mechanisms could be used, such as one or more detents disposed within autoinjector 100 that interface with one or more grooves on a piercing pin or other activation mechanism. Other activation impeding mechanisms may include a high friction surface coating that releasably impedes an activation mechanism, an elastic or otherwise deformable member that holds the activation mechanism in place and breaks when autoinjector 100 is activated using an appropriate method, a magnetic field that resists movement of a magnet attached to or otherwise connected with the activation mechanism, or any other mechanism suitable for releasably retaining a component and releasing it under predetermined conditions.

Gas escaping from gas cartridge 220 first pushes piercing pin 232 back against a piercing pin seal 264 located in a piercing pin housing 268 that is disposed within activation channel 112. As piercing pin seal 264 blocks air flow from passing through activation channel 112 in a proximal direction, the air is forced to flow around and towards the distal end of gas cartridge 220 to flow control orifice 240 (see, e.g., FIG. 5D). The gas flowing through flow control orifice 240 passes into medicament channel 116 of inner housing 108 via cross-channel coupling 120 and starts to fill the chamber behind a plunger seal 272 in syringe assembly 304, which forms a seal between syringe body 216 and pull rod 228. As this volume fills, inner housing 108 moves toward the back of the device (see FIGS. 5C and 5D). In some embodiments, syringe assembly 304 may be prevented from being pulled backward along with inner housing 108 toward the distal end of autoinjector 100 by one or more syringe body retainers that may be formed in outer housing 104 and extend through a slot in inner housing 108, which grip the syringe assembly at the location of a circumferential recess of the syringe assembly, as further described hereinbelow in the context of FIG. 7. As inner housing 108 moves backward, tension is applied to pull rod 228, which results in transfer valve expander 404 of the pull rod being pulled towards the distal end of flexible (e.g., rubber) transfer valve 224, which relaxes the seal around the transfer valve and, as the pull rod pulls the transfer valve backward toward the distal end of autoinjector 100, forces diluent 504 to flow around the transfer valve and forcefully mix with dried drug 500 to form a mixed drug 508 or medicament (see FIG. 5D).

After the diluent has mixed with the dried medication and pull rod 228 reaches the end of its distal motion relative to syringe body 216, the gas pressure behind plunger seal 272 continues to rise until sufficient gas pressure force is applied to release the pull rod from pull rod retainer 252, here a plastic or metal clip disposed on the distal side of an inner housing end cap 276 that grips a circumferential recess in the pull rod (see, e.g., FIGS. 2-4). Notably, in some embodiments, a material that breaks in the presence of a predetermined pressure gradient, such as a rod or string, may be used in place of or in addition to the illustrated metal clip design of pull rod retainer 252. In some embodiments, one or more burst disks, blow-off caps, pyrotechnic devices, and/or electronic triggers may be used to implement the pull rod retainer. In some embodiments, the pull rod itself may break when enough tension is applied to it in order to extend needle 212 and perform an injection. The time elapsed during this pressure rise provides a pause of a preconfigured duration, as discussed further hereinbelow, that allows mixed drug 508 to better dissolve or disperse within syringe body 216 such that it is suitable for injection. When the gas pressure behind plunger seal 272 reaches a predetermined level, pull rod 228 retainer 252 releases pull rod 228, and the pressure thrusts syringe assembly 304 forward to compress return spring 248 and extend needle 212 out of the autoinjector and, typically, into the injection site (see, e.g., FIG. 5E).

Figure 5E:
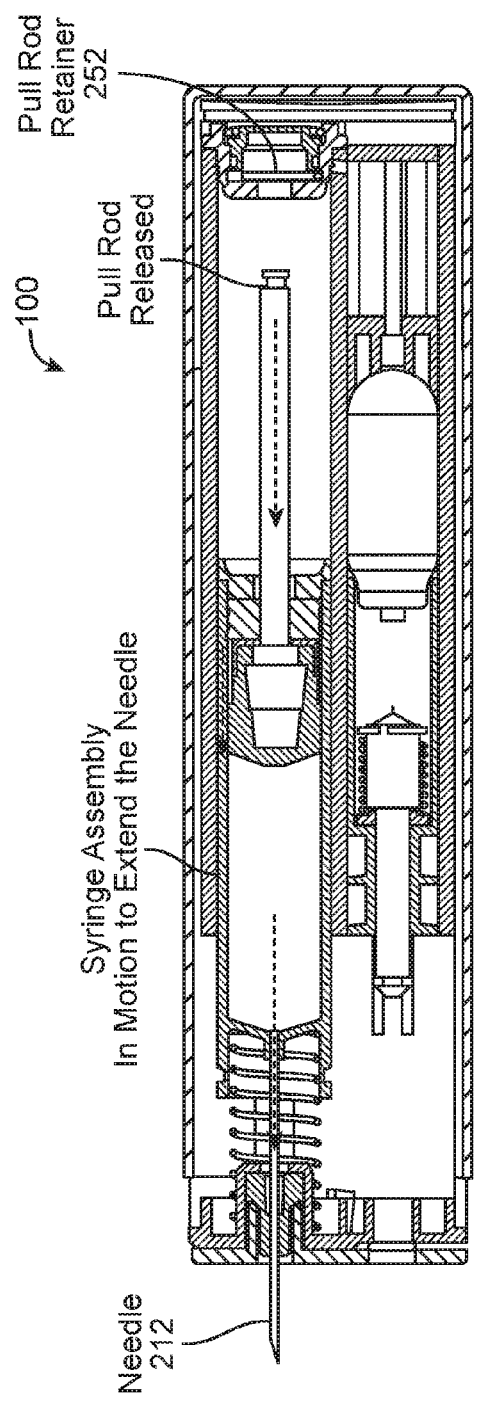
Figure 5F:
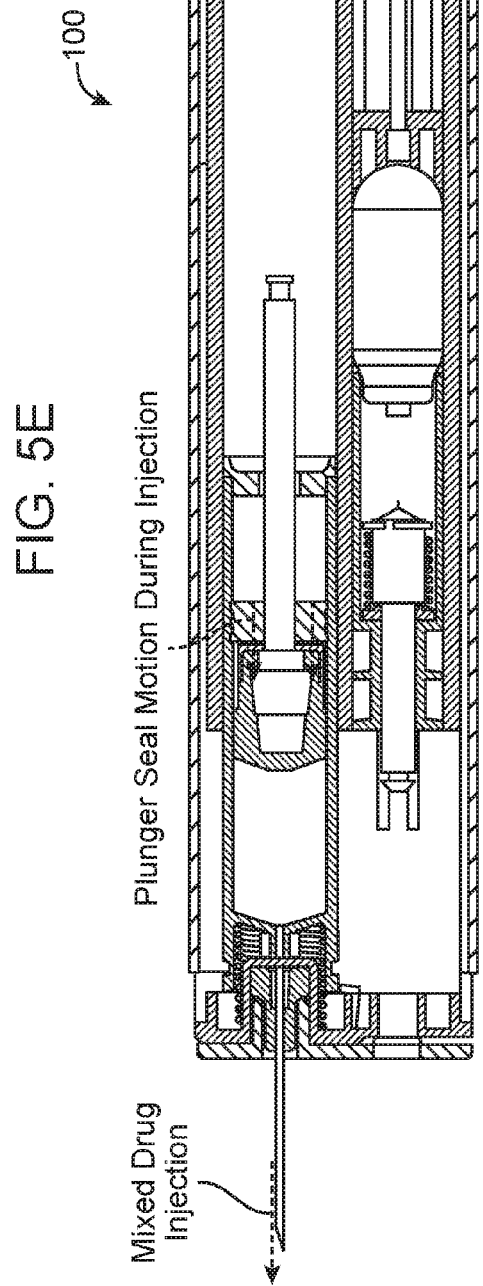
Figure 5I:
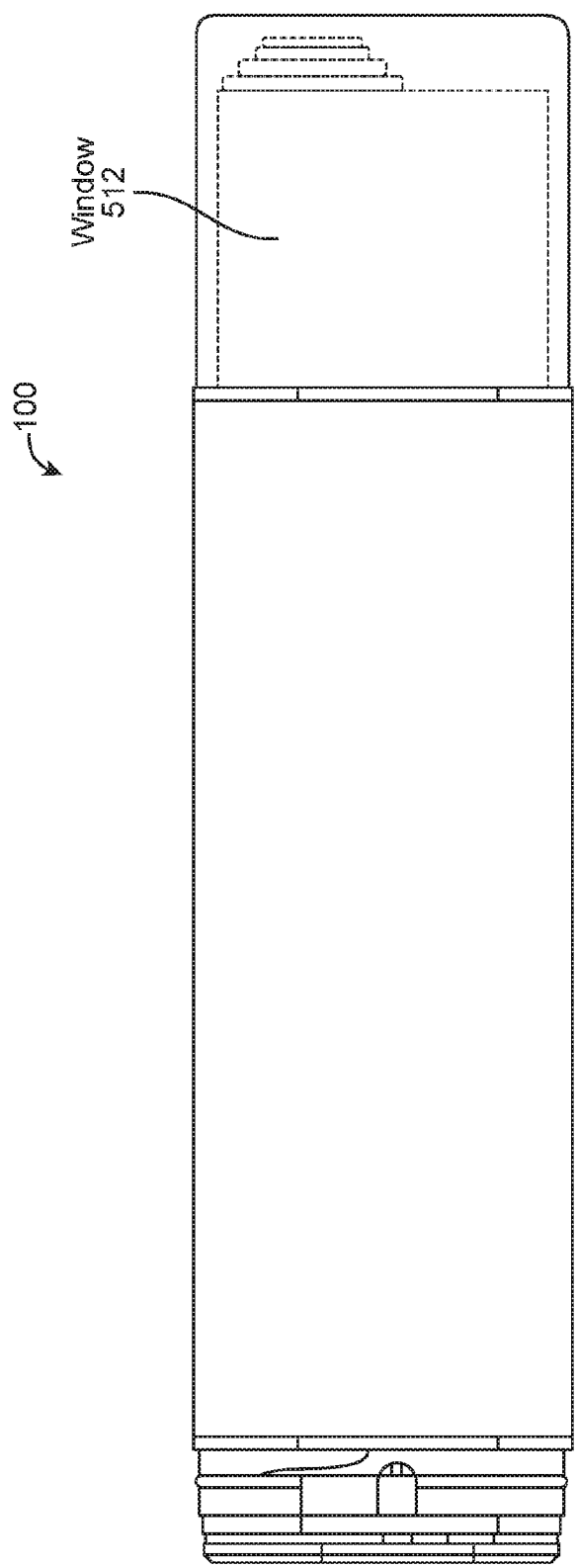
FIG. 5I is an exterior view of the pneumatic autoinjector of FIG. 1, illustrating a window located in the housing.

After needle 212 extension, the continued metering of compressed gas into the volume behind plunger seal 272 via flow control orifice 240 and cross-channel coupling 120 provides a pressure force that pushes the plunger seal forward to push mixed drug 508 out of the syringe through the needle and into the patient (see FIG. 5F). After completion of the medicament injection (i.e., when the plunger seal reaches the end of its travel), the metered gas continues to increase the pressure in the volume behind plunger seal 272 until pressure relief cap 256 opens (see FIG. 5G). This sudden opening of the pressure relief cap orifice releases gas and depressurizes the volume behind syringe assembly 304, which allows return spring 248 to push the syringe assembly, including needle 212, back inside the autoinjector inner housing for safe handling until disposal (see FIG. 5H). In some embodiments, inner housing 108 may provide recognizable indicia (e.g., bright red or orange material adhered to the external surface) that may be visible through a transparent window 512 (see, e.g., FIG. 5I) in the distal end of outer housing 104 of the autoinjector after the autoinjector has completed an injection sequence. The visible inner housing signals that the device is spent, as inner housing 108 is not visible during device storage (see, e.g., FIGS. 5A, 5H, and SI). In some embodiments, alternative methods of signaling that autoinjector 100 has been used or that a mixing phase is completed may be used. For example, such signals could occur when pressure relief cap 256 activates, which may produce a compressed gas actuated whistle through a properly configured and dimensioned orifice in the pressure relief cap or other portion of the autoinjector and/or an internal mechanical "click" sound and/or tactile vibration may be produced when the pull rod is released or injection is complete and the needle has been retracted into the outer housing. In some embodiments, an electronic switch may be activated within an autoinjector at one or more points during an injection sequence that may cause a sound or other feedback to be produced, a mechanism such as a pop-out indicator may be forcefully ejected, and/or a variety of other mechanisms may be used that may be actuated by compressed gas or otherwise.

Other components of autoinjector 100, as shown in FIG. 2, include: a front cover 280 of outer housing 104, which grips needle tip seal 244 and provides a surface on which piercing pin retainer 260 can rest prior to activation; a gas cartridge spacer 284, which helps to position various sizes of gas cartridge 220 and ensure proper timing of various stages of an autoinjector sequence by providing a buffer volume; and a gas flow slot 288 or similar path past the gas cartridge, which allows the passage of gas around the gas cartridge to the flow control orifice 240. Gas cartridge 220 may be secured in place in activation channel 112 with epoxy adhesive or mechanical restraint to ensure that gas cartridge 220 stays in place relative to activation channel 112 so that the gas cartridge is not accidentally punctured by piercing pin 232 prior to an intentional activation. In some embodiments, flow control orifice 240 and/or gas cartridge spacer 284 may be omitted. Further, in some embodiments, flow control orifice 240 may be provided at the location of cross-channel coupling 120. Further components of autoinjector 100, as shown in FIG. 3, include: pressure relief cap retainer 308, which holds pressure relief cap 256 in place prior to a pressure gradient forcing the pressure relief cap past the pressure relief cap retainer detent after an injection has taken place; a pressure relief cap seal 312, which ensures that no air can escape around the edges of the pressure relief cap prior to the pressure relief cap relieving the pressure in inner housing 108 after a predetermined interval in an injection sequence; and a piercing pin spring clip 316, which is received on a circumferential recess on the distal end of piercing pin 232 and enables activation spring 236 to actuate the piercing pin. Yet other components of autoinjector 100, as shown in FIG. 4, include: a syringe rear seal 408, which seals between syringe body 216 and the bore of inner housing 108 to prevent gas leakage past the syringe body; and a transfer valve stiffener 412, which helps to ensure that the expander is not pulled out of transfer valve 224 and that the transfer valve stays properly oriented within syringe body 216, particularly during mixing and injection stages of an injection sequence (see, e.g., FIGS. 5D-E). One of ordinary skill in the art will understand, after reading this disclosure in its entirety, that these and each of the other components described herein can be implemented in any number of ways, parts can be combined and formed monolithically or attached to one another through mechanical or other means, and various materials and modifications can be made to autoinjector 100 without departing from the spirit and scope of this disclosure, as further described hereinbelow.

Tunability and Experimental Results

Various aspects of autoinjector 100 provide design parameters that can be adjusted to tune the timing of device operation to suit the application need. Notably, this tunability is in addition to the customization that is inherently present in the design approach by changing device dimensions as needed to accommodate different injection volumes. These adjustable design parameters include the following: (1) gas cartridge 220 volume, (2) gas cartridge pressure, (3) flow control orifice 240 size, (4) sizing of the volume pressurized prior to pull rod 228 release, (5) pull rod retainer 252 release pressure/force, and (6) pressure relief cap 256 release pressure.

For example, gas cartridge 220 volume and charge pressure may be modified, e.g., by either increasing either (or both), which results in faster injection sequence execution, while, on the other hand, insufficient gas inventory (i.e., the arithmetic product of pressure and volume) results in incomplete device operation. Flow control orifice 240 and/or cross-channel coupling 120 size can be modified, e.g., increased to decrease flow restriction, which may result in faster injection sequence execution in some embodiments. The volume downstream of flow control orifice 240 that is pressurized prior to pull rod 228 release can be modified, e.g., increased, which increases the available hold time for medicament dissolution prior to needle 212 extension. The triggering force required to release pull rod 228 and enable needle 212 extension step can be modified, e.g., increased in order to increase the available hold time for medicament dissolution prior to needle 212 extension. Further, the triggering force required to open pressure relief cap 256 may be modified; increasing this force provides a larger pressure difference between the pressures required to trigger pull rod 228 release from pull rod retainer 252 and activation of the pressure relief cap, which can help to account for inaccuracies or inconsistencies in part performance, differences in atmospheric pressure, etc., and thus contribute to increased device reliability. However, increasing the triggering force required to open pressure relief cap 256 also increases the time required for the needle to retract after the injection, which may be undesirable in some instances. Other parameters that affect operation timing and forces include the amount of diluent and dried (or other) medicament predisposed in syringe body 216, friction, the spring constant (i.e., spring strength) of return spring 248, and the gas volume and sealing in the high pressure chamber (on the proximal side of flow control orifice 240) containing pressurized gas cartridge 220 and piercing pin 232.

A physics-based computer model of the autoinjector components was developed to predict the pressures, temperatures, gas flow rates, and gas volumes within autoinjector 100 as a function of time after high-pressure gas cartridge 220 is punctured by piercing pin 232. Pressures in gas cartridge 220 (V1) and behind the plunger seal (V2) were monitored during simulation of the computer model. The following parameters were used in the simulation: gas cartridge 220 volume; gas cartridge charge pressure; flow control orifice 240 diameter; pull rod retainer 252 release pressure; and pressure relief cap 256 activation pressure.

During simulation, once the high-pressure cartridge was pierced, its pressure dropped almost immediately as it pressurized the gas volume between gas cartridge 220 and flow control orifice 240. For one particular set of input parameter values, over the first 0.5 seconds, the gas flowed through flow control orifice 240 and expanded the volume behind plunger seal 272, which resulted in pull rod 228 being drawn through syringe body 216 and forcing the diluent and medicament to mix via transfer valve 224. The volume behind plunger seal 272 remained at a fixed value as pressure built to pull rod retainer 252 release pressure, which was reached about 3.0 seconds after activation. Once the rod was released, the V2 volume (pressurized volume in inner housing 108) expanded as needle 212 was rapidly extended. The medicament injection occurred from about three seconds after activation to six seconds after activation, at which time the V2 volume reached its maximum volume. Gas continued to flow through flow control orifice 240, and the pressure in the V2 volume continued to rise until it reached the pressure relief cap 256 activation pressure value at approximately 12 seconds after activation. Once pressure relief cap 256 activated, the pressure in the V2 volume dropped rapidly and return spring 248 pushed syringe assembly 304 back into inner housing 108.

Faster device operation can generally be achieved by increasing the gas flow rate into the volume behind plunger seal 272 by some combination of (1) increasing gas cartridge 220 volume, (2) increasing the gas cartridge charge pressure, and (3) increasing flow control orifice 240 diameter. A lower pull rod retainer 252 release pressure may also be used, but too low of a pressure can potentially lead to insufficient needle 212 extension. Pressure relief cap activation pressure must always be above the pull rod retainer 252 release pressure with sufficient margin to prevent inadvertent pressure relief prior to completion of medicament injection. Minimizing the difference between these two pressures also minimizes the time to needle 212 retraction.

Additional Features and Alternative Embodiments

Figure 6A:
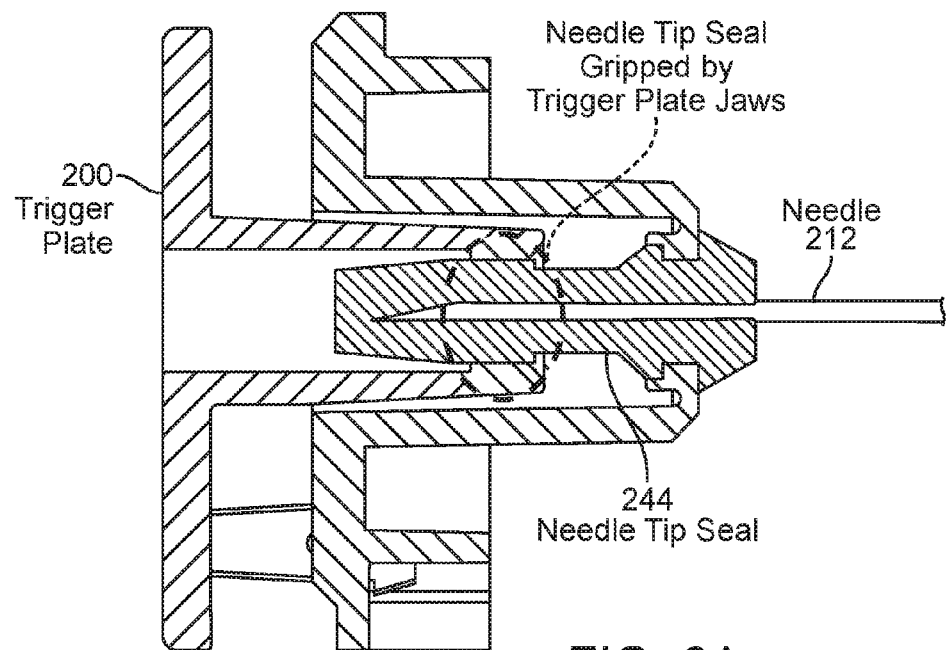
FIGS. 6A-B are cross-sectional plan views of a needle tip seal that may be used with a pneumatic autoinjector like that of FIG. 1.
Figure 6B:
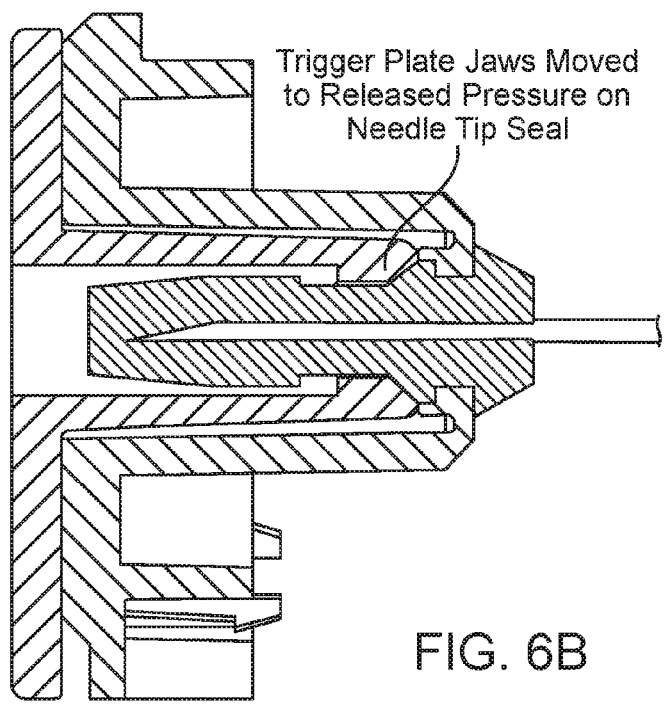

FIGS. 6A-B illustrate a mechanism for restraining or partially restraining an enclosed medication-filled syringe assembly, such as syringe assembly 304, by gripping the syringe assembly needle 212 in a flexible (e.g., rubber) needle tip seal 244. In FIG. 6A, a widened portion of needle tip seal 244 is shown being gripped by opposing jaw-like portions of trigger plate 200. As illustrated in FIG. 6B, the gripping force is released as the jaws slide past the wide section of needle tip seal 244 when trigger plate 200 is depressed, which may also trigger the autoinjector, as discussed hereinabove. In the absence of this gripping force, needle 212 of the syringe can more easily push through needle tip seal 244 and extend at the proper time when sufficient pneumatic force is applied from within the autoinjector.

Figure 7:
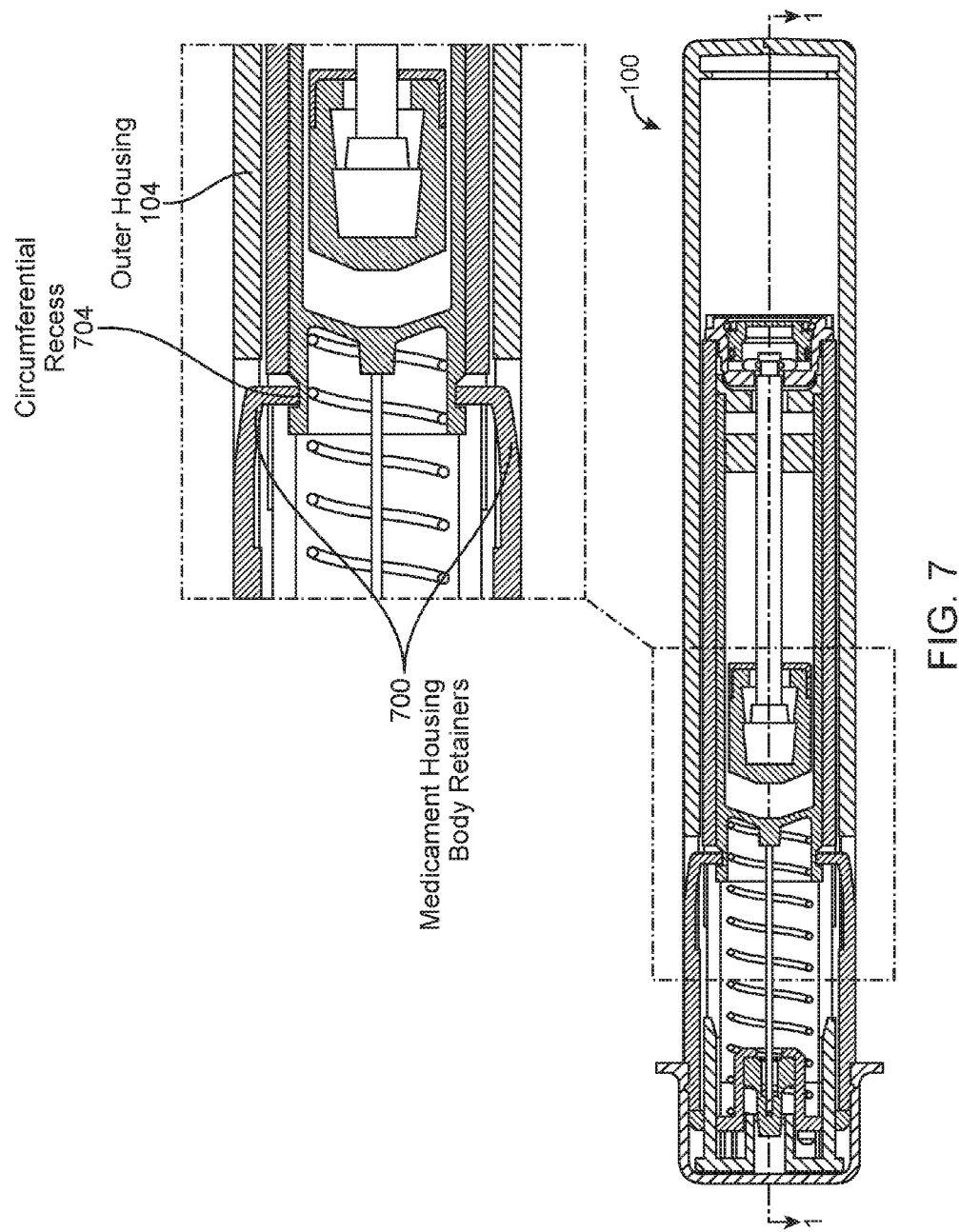
FIG. 7 is a cross-sectional plan view taken along line 7-7 of FIG. 1 illustrating the operation of medicament housing body retainers that help to ensure that the medicament housing body is held in place in the medicament channel of the pneumatic autoinjector of FIG. 1 prior to activation, during mixing, and after injection.

FIG. 7 provides additional detail regarding a method for securing a syringe assembly, such as syringe assembly 304, in place within an autoinjector to prevent it from dislodging during moderate mechanical shocks and/or vibrations. If not adequately secured by a return spring such as return spring 248, syringe assembly 304 could jog forward enough to (1) pierce needle tip seal 244, resulting in contamination of the sterile syringe environment; and/or (2) dislodge pull rod 228 and transfer valve 224, possibly resulting in diluent 504 leaking around the transfer valve into the storage chamber for dried drug 500 (or other medicament) in medicament chamber 400. As shown in FIG. 7, two medicament housing body retainers 700 may be molded into outer housing 104 near the front end of the device. In some embodiments, perforations created in outer housing 104 as a result of molding medicament housing body retainers 700 therein may be covered with an outer wrapping, such as a label, or otherwise hermetically sealed in such a way that intended movement of the retainers is not prevented. Further, in some embodiments, hard stops may be used as medicament housing body retainers, provided that syringe body 216 is keyed to slide forward into position during assembly and then, e.g., rotated to lock into the stops to prevent backward motion of the syringe body during drug mixing. As shown, one or more medicament housing body retainers 700 may extend through one or more slots in inner housing 108 (see, e.g., FIG. 3) and produce an inward force against a medicament housing body, such as syringe body 216. The proximal end of syringe body 216 may have a circumferential recess 704 into which medicament housing body retainers 700 snap. The proximal edge of recess 704 and the proximal and distal contact surfaces of medicament housing body retainers 700 may be flat surfaces roughly perpendicular to the longitudinal axis of medicament channel 116, as shown in FIG. 7. When medicament housing body retainers 700 are engaged in recess 704, the proximal edges of the retainers and the distal facing edge of the recess press against each other to mechanically prevent the syringe from moving backward (distally) under high forces.

The distal side of recess 704 in the medicament housing body has a sloped surface, which enables medicament housing body retainers 700 to slide up out of the recess when a relatively large forward force is applied to the syringe housing, such as that intentionally provided by needle 212 extension force of the autoinjector. However, the sloped rear surface of recess 704 and the compression force of medicament housing body retainers 700 are selected such that syringe body 216 cannot move forward in inner housing 108 under moderately low forces, such as the forward force generated when the autoinjector is dropped and lands on its proximal end. The co-action of medicament housing body retainers 700 and recess 704 thus prevents forward motion of syringe body 216 within inner housing 108 under moderate forward forces and high backward forces, but allows intentional forward motion of the syringe body (under high forward force) during needle 212 extension stage. It is important to note that if the retention force is too high, the autoinjector may begin ejecting the mixed medicament prior to extension of needle 212.

Figure 8A:
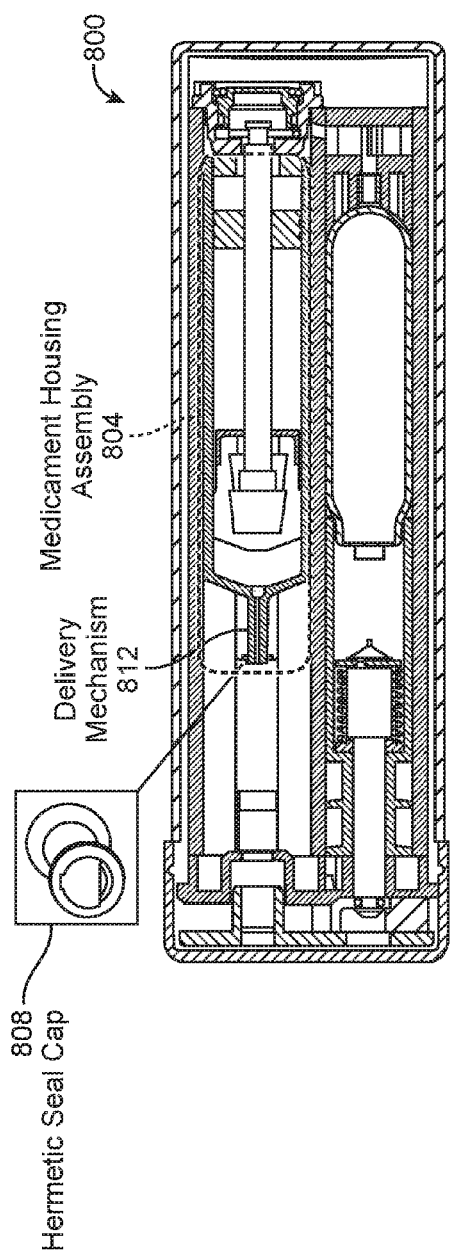
Figure 8B:
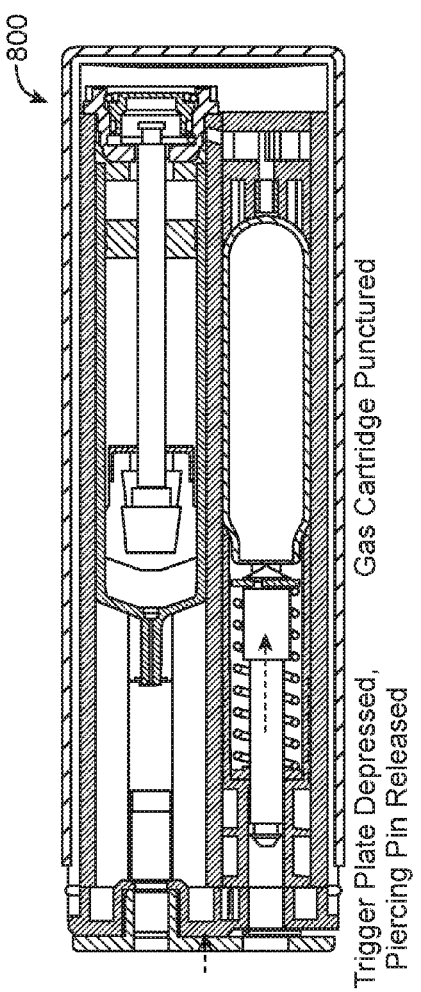

FIGS. 8A-F illustrate a needle-free autoinjector 800 implemented in accordance with various aspects of the present disclosure. Because needle-free autoinjector 800 operates based on many of the same principles as autoinjector 100 and using many very similar or identical components, primarily distinguishing aspects of the needle-free autoinjector are labeled in FIGS. 8A-F and discussed in detail hereinbelow. Notably, in some embodiments, an inner housing and outer housing of a needle-free autoinjector may be formed monolithically as a single housing. A storage condition of needle-free autoinjector 800 is shown in FIG. 8A with safety cap and safety lock in place, illustrating medicament housing assembly 804, hermetic seal cap 808, and needle-free high-pressure delivery mechanism 812. After removing the safety cap and safety lock, depressing the trigger plate releases the piercing pin, which punctures the gas cartridge (see FIG. 8B), just as with autoinjector 100. Gas pressure pushes the piercing pin against the piercing pin seal and expands the volume behind the plunger seal, pushing medicament housing assembly 804 forward while retaining the pull rod and transfer valve (see FIG. 8C). In some embodiments, this movement may result in hermetic seal cap 808 being removed or otherwise broken through interference with a portion of the trigger plate (see FIGS. 8C and 8D). This motion causes diluent to flow around the valve for medicament/diluent mixing. After mixing, the needle-free autoinjector sequence pauses while gas pressure continues rising behind medicament housing assembly 804 and the medicament and diluent homogenize and dissolve. Rising gas pressure increases tension on the pull rod, and, once the force is high enough, the pull rod releases and the gas pressure forces the plunger seal forward to eject the diluted medicament as a strong jet through delivery mechanism 812, which, in some embodiments, may result in hermetic seal cap 808 being broken or otherwise breached if it was not already removed by other means. After injection is complete, the pressure behind the plunger seal continues to rise until the pressure relief cap releases and vents to atmosphere. Notably, in some embodiments, the pressure relief cap may be omitted from autoinjector 800.

Those of ordinary skill in the art will recognize, after reading this disclosure in its entirety, that, although specific embodiments are disclosed herein, many variations on the inventive themes presented herein are realizable in view of the teachings of the present disclosure. For example, in some embodiments of an autoinjector like autoinjector 100 or needle-free autoinjector 800, the gas cartridge piercing pin may be: (1) manually pushed against the gas cartridge with enough force to puncture the cartridge without necessarily requiring an activation spring; (2) manually pushed against the cartridge using a mechanism that provides mechanical advantage, such as a lever; (3) forced against the gas cartridge by a nonmechanical force, such as a permanent magnet, induction coil (e.g., an electromagnet), or pressurized gas or water; or (4) pushed against the gas cartridge when the autoinjector is dropped under the force of gravity, among others.

Further, rather than using coil springs like those shown and described herein, leaf springs or any other appropriate biasing mechanisms may be used, such as chemical propellants. Further still, rather than using a trigger plate as part of an activation mechanism, a button could be used, either on the proximal surface or on a side of the autoinjector, to push the piercing pin retainer out of the way or otherwise activate the device, a nonplanar plate could be used, and/or a lever could be used in connection with the activation mechanism to decrease the amount of force required to activate the autoinjector. In some embodiments, the orientation of the gas cartridge and piercing pin may be reversed within the activation channel such that the piercing pin is located distal to the gas cartridge and directed in a proximal direction and the gas flows distally away from the gas cartridge. This may require (1) a piercing-pin-like component to be attached to or otherwise connected with the gas cartridge and a retainer that acts like a piercing pin retainer and (2) a larger or stronger activation spring to be used in order to provide sufficient force to drive the cartridge against the piercing pin in order to release the gas in the cartridge.

There are several combinations of medicaments or other materials that could be mixed in accordance with aspects of the present disclosure. Although a dried drug and diluent are used as examples in, e.g., FIG. 5A, any combination of dry/wet, liquid/liquid, gas/gas, liquid/gas, or dry/gas may be used, provided that at least one component is fluidic enough to pass around the transfer valve. Other materials that could be used include medications, vaccines, and other therapeutics, such as viral or cell treatments. Further, novel multi-component chemistries that must be mixed immediately before use, such as thin epoxies, substances resulting from chemical reactions, or chemical gas generators, may be produced using aspects of the present disclosure.

The foregoing has been a detailed description of illustrative embodiments of the invention. It is noted that in the present specification and claims appended hereto, conjunctive language such as is used in the phrases "at least one of X, Y and Z" and "one or more of X, Y, and Z," unless specifically stated or indicated otherwise, shall be taken to mean that each item in the conjunctive list can be present in any number exclusive of every other item in the list or in any number in combination with any or all other item(s) in the conjunctive list, each of which may also be present in any number. Applying this general rule, the conjunctive phrases in the foregoing examples in which the conjunctive list consists of X, Y, and Z shall each encompass: one or more of X; one or more of Y; one or more of Z; one or more of X and one or more of Y; one or more of Y and one or more of Z; one or more of X and one or more of Z; and one or more of X, one or more of Y and one or more of Z.

Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve aspects of the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An automatic injector for delivering a medicament, comprising:
    an outer housing having proximal and distal ends;
    an inner housing disposed within the outer housing, the inner housing containing an activation channel and a medicament channel, the activation and medicament channels having proximal and distal ends and the inner housing having a cross-channel coupling located proximate the distal ends of the activation and medicament channels that fluidly couples the activation and medicament channels;
    an activation mechanism; and
    an activation impeding mechanism,
    the activation channel comprising:
        a pressure-release mechanism associated with an activation spring;
        a flow control coupling located proximate the distal end of the activation channel and fluidly coupled with the medicament channel; and
        a pressurizable chamber containing a compressed gas, and
    the medicament channel comprising:
        a pull rod retainer and a pressure-relief mechanism located at the distal end of the medicament channel;
        a medicament housing assembly including a medicament delivery mechanism and a medicament housing body slidably disposed within the medicament channel,
        the medicament housing body including proximal and distal ends and comprising:
            a medicament chamber fluidly coupled with the medicament delivery mechanism and having proximal and distal ends;
            a valve disposed within the medicament chamber and separating two substances predisposed within the medicament chamber;
            a pull rod disposed within the medicament housing body and having proximal and distal ends, the distal end of the pull rod releasably coupled with the pull rod retainer and the proximal end of the pull rod coupled with the valve; and
            a plunger sealingly disposed about the pull rod within the medicament housing body.

2. An automatic injector according to claim 1, wherein the medicament channel further comprises a return spring biasing the medicament housing assembly away from the proximal end of the outer housing.

3. An automatic injector according to claim 2, wherein a sufficient amount of pressure applied against the activation mechanism results in:
    the activation mechanism overcoming the activation impeding mechanism;
    the activation spring urging the pressure-release mechanism and the pressurizable chamber together, enabling the compressed gas to escape from the pressurizable chamber;
    the gas from the pressurizable chamber passing through the flow control coupling and cross-channel coupling into a portion of the medicament channel between the plunger and the pressure-relief mechanism, causing the inner housing to move towards the distal end of the outer housing and pulling the pull rod through the medicament housing body, resulting in the valve moving to the distal end of the medicament housing body and causing the two substances to be mixed to create a medicament;
    the pressure of the gas from the pressurizable chamber causing the pull rod to be released from the pull rod retainer after an appropriate mixing time has elapsed and urging the medicament housing assembly against the return spring, causing the medicament delivery mechanism to extend from the proximal end of the outer housing and the plunger to force the medicament through the medicament delivery mechanism; and
    the pressure-relief mechanism opening after the medicament has been forced through the medicament delivery mechanism, relieving the pressure in the inner housing and enabling the return spring to urge the distal end of the inner housing towards the distal end of the outer housing and retract the medicament delivery mechanism into the outer housing.

4. An automatic injector according to claim 1, wherein a sufficient amount of pressure applied against the activation mechanism results in:
    the activation mechanism overcoming the activation impeding mechanism;
    the activation spring urging the pressure-release mechanism and the pressurizable chamber together, enabling the compressed gas to escape from the pressurizable chamber;

the gas from the pressurizable chamber passing through the flow control coupling and cross-channel coupling into a portion of the medicament channel between the plunger and the pressure-relief mechanism, causing the medicament housing assembly to move towards the proximal end of the outer housing and pulling the pull rod through the medicament housing body, resulting in the valve moving to the distal end of the medicament housing body and causing the two substances to be mixed to create a medicament;

the pressure of the gas from the pressurizable chamber causing the pull rod to be released from the pull rod retainer and the plunger to force the medicament through the medicament delivery mechanism after an appropriate mixing time has elapsed; and the pressure-relief mechanism opening after the medicament has been forced through the medicament delivery mechanism, relieving the pressure in the inner housing.

5. An automatic injector according to claim 4, wherein the inner housing and outer housing are formed monolithically as a single housing.

6. An automatic injector according to claim 1, wherein the outer housing includes a window proximate the distal end of the outer housing and the inner housing has a recognizable outer surface that is not visible through the window of the outer housing until the compressed gas escapes from the pressurizable chamber.

7. An automatic injector according to claim 1, wherein the pressure-relief mechanism is configured and dimensioned to produce a tactile vibration after opening.

8. An automatic injector according to claim 1, wherein the pressure-relief mechanism is configured and dimensioned to produce an audible signal after opening.

9. An automatic injector according to claim 1, further comprising a medicament delivery mechanism tip seal disposed within the proximal end of the outer housing including a widened portion and surrounding the medicament delivery mechanism, the activation mechanism further comprising opposing structures that grip the medicament delivery mechanism tip seal around the widened portion until a sufficient amount of pressure is applied against the activation mechanism to force the opposing structures past the widened portion.

10. An automatic injector according to claim 1, wherein a first one of the two substances is predisposed proximate the proximal end of the medicament chamber and comprises dry material, a liquid, or a gas and the other of the two substances is predisposed proximate the distal end of the medicament chamber and comprises a liquid, a liquid, or a gas, respectively.

11. An automatic injector according to claim 10, wherein the first one of the two substances comprises dry material and the other of the two substances comprises a liquid.

12. An automatic injector according to claim 1, further comprising:
a safety cap configured and dimensioned to fit over the proximal end of the outer housing and the activation mechanism; and
a spacer attached to the safety cap and located between the activation mechanism and the outer housing to prevent the activation mechanism from moving towards the outer housing until the safety cap is removed.

13. A method of tuning an automatic injector according to claim 1, the method comprising tailoring a retaining force of the pull rod retainer to set an appropriate mixing time for the two substances or to set an appropriate medicament delivery mechanism force, plunger force, or needle retraction time.

14. A method of tuning an automatic injector according to claim 13, further comprising tailoring a flow rate for the flow control coupling and/or cross-channel coupling to set an appropriate mixing time for the two substances or to set an appropriate medicament delivery mechanism force, plunger force, or needle retraction time.

15. A method of tuning an automatic injector according to claim 1, the method comprising tailoring a flow rate for the flow control coupling and/or cross-channel coupling to set an appropriate mixing time for the two substances or to set an appropriate medicament delivery mechanism force, plunger force, or needle retraction time.

16. A method of tuning an automatic injector according to claim 1, the method comprising tailoring a volume of one or more buffer volumes in the automatic injector in order to set an appropriate medicament mixing duration or needle retraction time.

17. A method of tuning an automatic injector according to claim 1, the method comprising tailoring one or more of a volume of gas in the pressurizable chamber, a pressure of gas in the pressurizable chamber, and a pressure at which the pressure-relief mechanism opens in order to set an appropriate medicament delivery duration or needle retraction time.

18. A method of tuning an automatic injector according to claim 1, the method comprising tailoring an activation impeding force of the activation impeding mechanism to set an appropriate trigger force for the activation mechanism.

* * * * *